United States Patent

Kanazawa et al.

[11] Patent Number: 5,366,727
[45] Date of Patent: Nov. 22, 1994

[54] ANTIBACTERIAL AGENT

[75] Inventors: Akihiko Kanazawa, Tokyo; Takeshi Endo; Tomiki Ikeda, both of Yokohama, all of Japan

[73] Assignee: Nippon Chemical Industrial Co., Ltd., Tokyo, Japan

[21] Appl. No.: 937,846

[22] PCT Filed: Feb. 21, 1992

[86] PCT No.: PCT/JP92/00187
§ 371 Date: Oct. 21, 1992
§ 102(e) Date: Oct. 21, 1992

[87] PCT Pub. No.: WO92/14365
PCT Pub. Date: Sep. 3, 1992

[30] Foreign Application Priority Data

Feb. 21, 1991 [JP] Japan .................. 3-047289
Feb. 21, 1991 [JP] Japan .................. 3-047290
Aug. 30, 1991 [JP] Japan .................. 3-244313

[51] Int. Cl.⁵ .................. A61K 31/80; A61K 31/66
[52] U.S. Cl. .................. 424/78.35; 424/78.31; 424/78.32; 424/405; 424/409; 526/274; 526/278; 568/8; 568/11; 514/134
[58] Field of Search .................. 526/274, 278; 568/8, 568/11; 424/78.31, 78.32, 78.35, 405, 409; 514/134

[56] References Cited

U.S. PATENT DOCUMENTS 3,065,272 11/1962 Garner et al. .
3,539,684 11/1970 Hoover .................. 424/78.35
4,749,642 6/1988 Kurematsu et al. .................. 430/372
4,855,211 8/1989 Janssens et al. .................. 430/213

FOREIGN PATENT DOCUMENTS 48-19309 6/1973 Japan .
50-5535 1/1975 Japan .
288547 12/1970 U.S.S.R. .
WO91/03938 4/1991 WIPO .

Primary Examiner—Mark Nagumo
Attorney, Agent, or Firm—Oblon, Spivak, McClelland, Maier & Neustadt

[57] ABSTRACT

An antibacterial agent comprising as an active ingredient a vinylbenzyl phosphonium salt of the general formula (I),

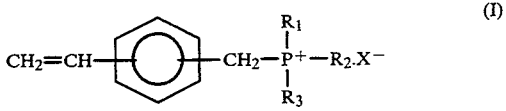

wherein $R_1$, $R_2$ and $R_3$ each represent a hydrogen atom, a linear or branched alkyl group having 1 to 18 carbon atoms, an aryl group, a hydroxyl group, or an alkoxyl-substituted alkyl, aryl or aralkyl group, and $X^-$ is an anion; and/or a phosphonium salt polymer in which the vinylbenzyl phosphonium salt, a monomer, is polymerized.

4 Claims, No Drawings

ANTIBACTERIAL AGENT

TECHNICAL FIELD

The present invention relates to antibacterial agents and, more particularly, to antibacterial agents comprising as active ingredients a phosphonium salt having vinyl groups and/or a phosphonium salt polymer in which the phosphonium salt, a monomer, is polymerized.

BACKGROUND ART

Recently, a variety of antibacterial agents have been used in the fields of industry, agriculture, food processing industry and the like.

Although the greater part of the synthesized antibacterial agents previously used have been highly toxic, research has progressed towards antibacterial agents with decreased toxicity, to develop polymer type immobilized antibacterial agents that are water-insoluble and have little toxicity. These immobilized antibacterial agents can confer antibacterial activity on the surface of various materials, and thus have been used in different fields including the textile industry where, for example antibacterial agents are immobilized on the surface of antibacterial and deodorant textiles.

It is reported that in the immobilized polymer type antibacterial agents, the antibacterial agents themselves are immobilized in pendant form to polymers such as polyvinyl, polyacrylate, polymethacrylate, polyester and polyamide. For example, alkyl pyridinium salts and alkyl dimethylbenzyl ammonium salts are immobilized by polyvinyl chains, biganides by polyacrylate chains and polymethacrylate chains, and alkyl pyridinium salts by polyester chains and polyamide chains.

Most of the immobilized antibacterial agents practically used or being researched are those of quaternary ammonium salts.

Further, certain type of phosphonium salt compound are known as biologically active substances which have a broad antibacterial spectrum against bacteria, fungi and algae such as various nitrogen-containing compounds (Japanese Patent Laid-Open Nos.57-204286, 63-60903, 1-93596, 2-240090, and 62-114903).

Although the quaternary ammonium salt type immobilized antibacterial agents have a broad antibacterial spectrum, they do not have sufficient antibacterial activity for short periods of exposure to affect microorganisms. Phosphonium salt compound type antibacterial agents also do not have sufficient antibacterial activity, and vinylbenzyl phosphonium salt compounds according to the present invention have not yet been disclosed.

DISCLOSURE OF THE INVENTION

Accordingly, an object of the present invention is to overcome the above mentioned problems and to provide antibacterial agents which have a broad antibacterial spectrum, and have sufficient antibacterial activity through a short period of exposure.

As a result of intensive research, the present inventors have now found that certain kinds of phosphonium salt compound type antibacterial agents having vinyl groups can solve the above mentioned problems.

That is, in a first aspect of the present invention, there is provided an antibacterial agent comprising as an active ingredient a vinylbenzyl phosphonium salt of the general formula (I),

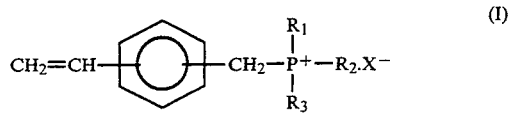

wherein $R_1$, $R_2$ and $R_3$ each represent a hydrogen atom, a linear or branched alkyl group having 1 to 18 carbon atoms, an aryl group, a hydroxyl group, or an alkoxyl-substituted alkyl, aryl or aralkyl group, and $X^-$ is an anion; and/or a phosphonium salt polymer in which the vinylbenzyl phosphonium salt, a monomer, is polymerized.

In a second aspect of the present invention, there is provided the above mentioned antibacterial agent in which a phosphonium salt polymer is a homopolymer of phosphonium salt of the general formula (II),

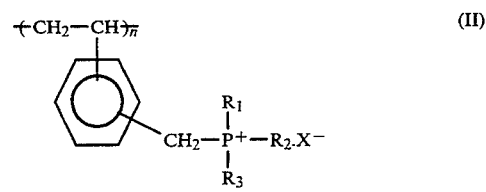

wherein $R_1$, $R_2$ and $R_3$ each represent a hydrogen atom, a linear or branched alkyl group having 1 to 18 carbon atoms, an aryl group, a hydroxyl group, or an alkoxyl-substituted alkyl, aryl or aralkyl group; $X^-$ is an anion; and n is an integer of 2 or more.

In a third aspect of the present invention, there is provided the above mentioned antibacterial agent in which the phosphonium salt polymer is a copolymer, whose degree of polymerization is 2 or more, and consists of 1 to 99 mole % of structural units of the general formula (III),

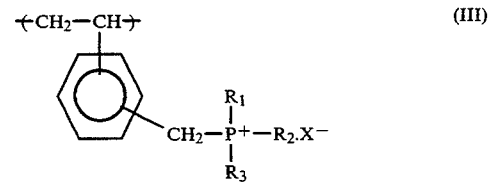

wherein $R_1$, $R_2$ and $R_3$ each represent a hydrogen atom, a linear or branched alkyl group having 1 to 18 atoms, an aryl or a aralkyl group, and the alkyl, aryl and aralkyl groups are possibly hydroxyl- or alkoxyl-substituted, $X^-$ is an anion; and 99 to 1 mole % of structural units of the general formula (IV),

wherein $R_4$ represents a hydrogen atom, a linear or branched alkyl having 1 to 4 carbon atoms, substituted or unsubstituted phenyl, amido, nitrile, pyridinyl, hydroxyl, acetoxyl, alkoxyl or carbazolyl group, lactam, or chain carboxylic acid and derivatives thereof.

DETAILED DESCRIPTION OF THE INVENTION

The present invention will be further illustrated below.

The antibacterial agent of the present invention comprises, as an active ingredient, a vinylbenzyl phosphonium salt per se of the above mentioned formula (I), and/or a homopolymer in which the compound of the above mentioned formula (I), a monomer, is polymerized, or a copolymer in which the compounds of above mentioned formula (I) and another vinyl compound monomer capable of copolymerizing with the compound of formula (I) are polymerized.

(Vinylbenzyl Phosphonium Salt)

Vinylbenzyl phosphonium salt one of the active ingredients in the antibacterial agent of the present invention, is the compound of formula (I). Examples of $R_1$, $R_2$ and $R_3$ in the formula (I) include alkyl groups such as methyl, ethyl, propyl, butyl, pentyl, hexyl, heptyl, octyl and dodecyl groups; aryl groups such as phenyl, tolyl and xylyl groups; aralkyl groups such as benzyl and phenytyl groups; those having hydroxyl-, alkoxyl-, and other-substituted groups; preferably alkyl groups such as heptyl and octyl groups; aryl groups such as phenyl and tolyl groups; and more preferably octyl and phenyl groups. $R_1$, $R_2$ and $R_3$ may be the same or different groups.

Where $R_1$, $R_2$ and $R_3$ are lower alkyl groups such as ethyl or butyl groups, the antibacterial agent is soluble in water and is dissolved in organic solvents such as alcohol and the like. In contrast, where $R_1$, $R_2$ and $R_3$ are a higher alkyl groups such as pentyl, hexyl or octyl groups, the solubility of the antibacterial agent to water decreases. Examples of $X^-$, an anion, include halogen ions such as fluorine, chlorine, bromine or iodine; carboxyl ions such as formic acid, acetic acid or oxalic acid; sulfuric acid ions, phosphoric acid ions, methyl or dimethyl phosphoric acid ions, ethyl or diethyl phosphoric acid ions, antimony fluoride ions, phosphorus fluoride ions, arsenic fluoride ions, boron fluoride ions, perchloric acid ions and the like. Among them, halogen ions are preferred.

Where $X^-$ is an antimony fluoride ion, phosphorus fluoride ion, arsenic fluoride ion, boron fluoride ion or perchloric acid ion, the compound in which $R_1$, $R_2$ and $R_3$ are any group becomes insoluble in water.

That is, the antibacterial agent of the present invention can be prepared as a water-soluble, water dispersible or water-insoluble antibacterial agent by changing the groups of $R_1$, $R_2$ and $R_3$, and $X^-$ depending their use.

Vinylbenzyl phosphonium salts of the formula (I) in which one of $R_1$, $R_2$ and $R_3$ is different from the other two tend to have greater antibacterial activity than that in which $R_1$, $R_2$ and $R_3$ are all the same. Further the compound tends to have greater antibacterial activity when $R_1$, $R_2$ and $R_3$ is 6 or more carbon atoms irrespective of being the same or different, and particularly these groups are octyl or more in cases of alkyl groups.

Examples of such vinylbenzyl phosphonium salts include octyldiethyl-3 (and-4)-vinylbenzyl phosphonium chloride, octyldibuthyl-3 (and-4)-vinylbenzyl phosphonium chloride, triphenyl-3 (and-4)-vinylbenzyl phosphonium chloride, dodecylphenyl-3 (and-4)-vinylbenzyl phosphonium chloride, trioctyl-3 (and-4)-vinylbenzyl phosphonium chloride, octyldiethyl-3 (and-4)-vinylbenzyl phosphonium bromide, octyldibutyl-3 (and-4)-vinylbenzyl phosphonium bromide, triphenyl-3 (and-4)-vinylbenzyl phosphonium bromide, dodecyldiphenyl-3 (and-4)-vinylbenzyl phosphonium bromide, trioctyl-3 (and-4)-vinylbenzyl phosphonium bromide, octyldibutyl-3 (and-4)-vinylbenzyl phosphonium tetrafluoroborate, trioctyl-3 (and-4)-vinylbenzyl phosphonium tetrafluoroborate, trioctyl-3 (and-4)-vinylbenzyl phosphonium perchlorate, trioctyl-3 (and-4)-vinylbenzyl phosphonium hexafluorophosphate and the like.

(Homopolymers in which Vinylbenzyl Phosphonium Salt is a Monomer)

The antibacterial agent of the present invention can further comprise as an active ingredient a phosphonium salt vinylpolymer in which a vinylbenzyl phosphonium salt of the above mentioned formula (I), a monomer, is homopolymerized, as shown in formula (II).

The phosphonium salt vinylpolymer of formula (II) is a homopolymer in which the vinylbenzyl phosphonium salt of the above formula (I), a monomer, is polymerized.

Examples of $R_1$, $R_2$ and $R_3$, and X are the same as those in the above mentioned vinylbenzyl phosphonium salt.

(Copolymers of a Vinylbenzyl Phosphonium Salt and a Vinyl Compound Monomer Copolymerizable therewith)

The antibacterial agent of the present invention can further comprises as an active ingredient the above mentioned phosphonium salt vinylpolymer in which the vinylbenzyl phosphonium salt of the formula (III) and the vinyl compound monomer (IV) are copolymerized a structural units.

In formula (III), examples of $R_1$, $R_2$ and $R_3$, and X are the same as those in the above mentioned vinylbenzyl phosphonium salt.

Examples of $R_4$ include hydrogen, halogens such as chlorine, bromine and iodine; linear or branched alkyl groups having 1 to 4 carbon atoms such as methyl, ethyl and butyl; substituted or unsubstituted phenyl groups such as phenyl, p-methylbenzene and tolyl-1,4-divinylbenzene; amido groups such as carbonamido and acrylamide; lactams such as N-vinyl-2-pyrrolidone and the like; chain carboxylic acids and derivatives thereof such as carboxyl, methoxycarbonyl and ethoxycarbonyl; nitrile groups; pyridinyl groups; hydroxyl groups; acetoxy groups; alkoxy groups such as methoxy and ethoxy. Examples of other vinyl compound monomers capable of copolymerizing with these vinylbenzyl phosphonium salts include unsaturated monocarboxylic acids such as acrylic acid and methacrylic acid; unsaturated dicarboxylic acids such as maleic acid and the like and lower alkylesters thereof; for example, derivatives such as methyl methacrylate and amidometalic salt; and acrylonitrile, vinyl acetate, ethylene, propylene, isobutylene, diisobutylene, isoprene, chloroprene, vinyl chloride, vinylpyrrolidine, N-vinyl-2-pyrrolidone and styrene, pyridine, acrylamide, and carbazole. One or more of them may be used.

METHOD FOR PREPARING THE ANTIBACTERIAL AGENTS OF THE PRESENT INVENTION

Although the antibacterial agent may be prepared by any method, some industrial scale preparation methods are illustrated below.

[1] Method for Preparing Vinylbenzyl Phosphonium Salts

The vinylbenzyl phosphonium salts of the present invention can be obtained by reacting styrene derivatives of the general formula,

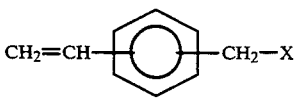

wherein X is halogen, or inorganic or organic acid residues and the like, and trialkyl phosphine of the general formula,

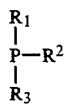

wherein $R_1$, $R_2$ and $R_3$ have the same meanings as mentioned above.

The reaction may be performed in the presence of an organic solvent and a polymerization inhibitor at a temperature of 25° to 110° C., preferably at the boiling point of the solvent for 1 hour or more.

Further a styrene derivative may be used in a range between equimolar and 2-fold molar concentrations relative to those of a phosphine derivative.

After completion of the reaction, a precipitate separated out was collected to obtain the desired product.

Appropriate solvents include n-hexane, toluene and the like, and polymerization inhibitors include hydroquinone, cathecol and the like.

[2] Method Method for Preparing Phosphonium Salt Vinyl Polymers and Copolymers

Industrial scale methods for preparing phosphonium salt vinyl polymers will be illustrated below though the preparation processes themselves are not limited thereby.

(Homopolymerization)

To a solvent is added the above mentioned vinylbenzyl phosphonium salt as a monomer, and then polymerization initiators. Examples of the solvent include water, methanol, ethanol, dimethylformamide, benzene, toluene or a mixture thereof. Examples of the polymerization initiator include 2,2'-azobisisobutyl nitrile, 2,2'-azobis-(2-aminopropane)hydrochloride, benzoyl peroxide, t-butylhydroperoxide, and the like.

The reaction temperature and the reaction time depend on the kinds of polymerization initiators. For example, the reaction temperature is preferably in a range of 40° to 100° C., and the reaction time is 0.5 hour or more, preferably 1 to 24 hours. Further the reaction is preferably conducted under increased or normal pressure and in an inert atmosphere. After completion of the reaction, the reaction mixture is poured into a large amount of acetone, or tetrahydorofuran, diethyl ether or n-hexane, and then any precipitate separated out is collected to obtain the polymer of the present invention. The degree of polymerization depends mainly on the kinds of reagents and the reaction conditions, and higher degrees of polymerization exert preferably greater antibacterial activity, without any limitations. Therefore, the degree may be 2 or more, and preferably in a range of about 10 to 500.

Although there is another method for preparation in which chloromethyl styrene is polymerized by the conventional method, and then functional groups of the polymer chain are converted to phosphonium salts, the former method for preparing the antibacterial agent of the present invention is preferred in order to obtain more homogeneous polymers.

(Copolymerization)

This polymerization method is easily conducted in the form of a random, block or graft polymerization by the above mentioned method or conventional methods for polymerizaiton, in which a mixture of the above mentioned vinylbenzyl phosphonium salt (III) and the above mentioned other vinyl monomer (IV), a monomer, copolymerizable therewith is used.

The compounded ratio of the compound (III) and the compound (IV) is, without any limitations, in a range of 1-99 mole %, preferably 1-70 mole % and more preferably 5-50 mole % of the compound (III), and 99-1 mole %, preferably 99-30 mole % and more preferably 95-50 mole % of the compound (IV).

The use of less than 1 mole % of the structural unit of the general formula (III) leads to a decrease in antibacterial activity, while the use of more than 99 mole % of that is not preferred from an economic aspect because of the presence of more than the required amount of units for antibacterial activity.

To a solvent are usually added 0.1-5 mole %, and preferably 0.2-2 mole % relative to the monomer of the same polymerization initiator as used in the above mentioned homopolymerization. The same conditions such as temperature and time in the polymerization are used as in the above mentioned homopolymerization.

There is also another method for preparing the phosphonium, salt vinyl copolymer of the present invention, in which chloromethyl styrene is polymerized with the above mentioned compound (I) by the conventional method and then functional groups of the polymer chain are converted to phosphonium salts.

Further there is another method in which after styrene, chloromethyl styrene and as a cross linking agent divinyl benzene are individually dissolved in a solvent, the above mentioned polymerization initiator is added, and then functional groups of the polymer chain are converted to phosphonium salts. This polymer with a three dimensional structure is insoluble in any solvent and has higher strength.

The degree of polymerization of the polymers depends exclusively on the kinds of monomers and polymerization conditions, and polymers having a higher degree of polymerization are preferred in terms of antibacterial activity, without any limitations. Thus, the degree of polymerization may be 2 or more, generally 2-1000 and preferably 10-500 for both homopolymers and copolymers.

The antibacterial agent of the present invention comprises the above mentioned monomer and/or polymer of vinylbenzyl phosphonium salt as an active ingredient, though the polymer type is widely applied compared to the monomer type because of the limited types, and lesser stability and antibacterial activity of the monomer type compounds.

However, it goes without saying that the monomer type has sufficient practicality depending on its intended.

Since the antibacterial agent of the present invention may be soluble in water or oil whether the vinylbenzyl phosphonium salt compounds are polymers or not, the antibacterial agent is able to be prepared in any form of solution, hydrate, emulsion or powder with desired carriers such as solvents or powders, as well as in the powdery form of the compound per se depending on the use. Examples of carriers include liquids such as water, alcohol, acetone, benzene, xylene, and carbon tetrachloride; organic solids such as higher alcohol, fats and oils, paraffin and DOP; and inorganic powders such as talc, kaolin, silica, alumina, magnesia and titanium dioxide.

Further, the preparation may comprise auxiliaries such as detergents, binding agents, coloring materials, dispersants and wetting agents, and other organic or inorganic antibacterial agents.

The antibacterial agent of the present invention has a broad antibacterial spectrum against various bacteria, fungi, algae, virus and the like, and particularly shows remarkable antibacterial activity against bacteria. Moreover, the antibacterial agent is heat stable even in comparison with quaternary ammonium salts and other organic compounds. For example, a vinylbenzyl phosphonium salt with phenyl groups has a decomposition temperature of about 250° C. The antibacterial activity, i.e. minimum inhibitory concentration (MIC), of an antibacterial agent according to the present invention varies depending on kinds and preparations of vinylbenzyl phosphonium salts, or kinds and growth environments of various microorganisms, though the antibacterial agent exerts its MIC at a concentration of 1 ppm or more of a phosphonium salt compound and generally has stronger antibacterial activity than well known antibacterial agents of quaternary ammonium salt.

The antibacterial agents of the present invention in accordance with forms of preparations can provide, for example, slime-preventive properties in the paper industry, or antiseptic and antibacterial properties to control materials, water, fats and oils, emulsions, paper, timber, gum, plastics, fiber, film, and coating compounds in various fields of industry.

Moreover, in a practical embodiment of the antibacterial agent of the above mentioned vinylbenzyl phosphonium salt monomer, antibacterial activity may be conferred on the antibacterial agents by conducting photo-graft polymerization of the vinylbenzyl phosphonium salt monomer using a high pressure mercury vapor lamp with, for example, benzophenone as a sensitizer, and then by conducting graft polymerization on the surface of a polymer base such as polypropyrene.

The antibacterial agents of the present invention whose mechanisms are not known in detail have greater antibacterial activity than previous antibacterial agents of quaternary ammonium salt, and these agents are thought to have the following effects.

(1) The cationic properties of the phosphonium salt allow increases in the concentration of the phosphonium salt on the vicinity of cell membranes having a negative charge, and thus the polymerization further increases the antibacterial activity.

(2) Pharmacological studies indicate that the phosphonium salt need not be incorporated into microorganisms because the salt is a cell membrane-attacking type antibacterial agent. Therefore, the decreased permeability to cell membranes by polymerization of the phosphonium salt is not a disadvantageous factor, but rather the effect of (1) above provides an advantageous polymeric effect.

BEST MODE FOR CARRYING OUT THE INVENTION

The present invention is further illustrated below.

Reference Example 1

(Synthesis of Vinylbenzyl Phosphonium Salt)
Samples 1-7

To a 100 ml flask undergoing sufficient nitrogen replacement were added 9.85 g (0.065 mole) of chloromethylstyrene and 10.88 g (0.054 mole) of tributyl phosphine, and then 20 ml of n-hexane. These compounds were reacted at 25° C. in the flask for 24 hours to obtain a white crystalline product. This crystalline product was filtrated and washed well using n-hexane. The resulting product was dried under reduced pressure at room temperature to obtain 8.84 g of tributyl-3 (and 4)-vinylbenzyl phosphonium chloride.

Then, the same procedure was conducted using a variety of phosphine derivatives in place of tributyl phosphine to obtain the various vinylbenzyl phosphonium salt compounds shown in Table 1.

TABLE 1

| Sample No. | Phosphine Derivative | Compound of Formula (I) |
|---|---|---|
| 1 | triethyl phosphine | triethyl-3 (and 4)-vinylbenzyl phosphonium chloride |
| 2 | tributyl phosphine | tributyl-3 (and 4)-vinylbenzyl phosphonium chloride |
| 3 | triphenyl phosphine | triphenyl-3 (and 4)-vinylbenzyl phosphonium chloride |
| 4 | trioctyl phosphine | trioctyl-3 (and 4)-vinylbenzyl phosphonium chloride |
| 5 | octyldiethyl phosphine | octyldiethyl-3 (and 4)-vinylbenzyl phosphonium chloride |
| 6 | octyldibutyl phosphine | octyldibutyl-3 (and 4)-vinylbenzyl phosphonium chloride |
| 7 | dodecyldiphenyl phosphine | dodecyldiphenyl-3 (and 4)-vinylbenzyl phosphonium chloride |

Examples 1-7

*Staphylococcus aureus* (IFO 12732) as a typical Gram-positive bacteria and *Escherichia coli* (IFO 3806) as a typical Gram-negative bacteria were exposed by the samples of the various vinylbenzyl phosphonium chlorides obtained from Reference Example 1 at the different concentrations and exposure time shown in Tables 2 and 3. The resulting antibacterial activity is shown in Table 2 and 3. The antibacterial activity was evaluated by the serial dilution method described below. Depending on exposure time, the more remarkable a decrease in the number of bacteria was, the stronger the antibacterial activity shown.

Serial dilution method: After 2 ml of a bacterial solution of $10^8$ bacteria/ml are inoculated into 18 ml of physiological saline, 2000 µg, 200 µg and 20 µg of various vinylbenzyl phosphonium salt compounds are exposed, and then the number of bacteria is measured. Depending on exposure time, the more remarkable a decrease in the number of bacteria was, the stronger the antibacterial activity shown. The numbers in the Tables are those of bacteria (bacteria/ml).

TABLE 2

Results of antibacterial activity test against *Staphylococcus aureus* (IFO 12732)
(No. of bacteria /ml)

| Sample No. | Compound of Formula (I) | Concentration of Compound | Exposure Time (hours) | | | |
|---|---|---|---|---|---|---|
| | | | 0 | 0.5 | 1.0 | 2.0 |
| 1 | ($R_1 = R_2 = R_3$ = ethyl group) (X = Cl) | 1 ppm | $6.5 \times 10^6$ | $10.8 \times 10^6$ | $6.3 \times 10^6$ | $9.7 \times 10^6$ |
| | | 10 ppm | $6.5 \times 10^6$ | $8.9 \times 10^6$ | $6.9 \times 10^6$ | $6.3 \times 10^6$ |
| | | 100 ppm | $6.5 \times 10^6$ | $10.8 \times 10^5$ | $12.0 \times 10^4$ | $7.6 \times 10^3$ |
| 2 | ($R_1 = R_2 = R_3$ = butyl group) (X = Cl) | 1 ppm | $6.5 \times 10^6$ | $9.1 \times 10^6$ | $6.2 \times 10^6$ | $4.6 \times 10^6$ |
| | | 10 ppm | $6.5 \times 10^6$ | $7.7 \times 10^6$ | $7.8 \times 10^5$ | $7.0 \times 10^4$ |
| | | 100 ppm | $6.5 \times 10^6$ | $6.6 \times 10^4$ | $7.1 \times 10^3$ | $8.0 \times 10^3$ |
| 3 | ($R_1 = R_2 = R_3$ = phenyl group) (X = Cl) | 1 ppm | $5.1 \times 10^6$ | $9.6 \times 10^6$ | $9.7 \times 10^6$ | $9.9 \times 10^6$ |
| | | 10 ppm | $5.1 \times 10^6$ | $10.3 \times 10^5$ | $8.3 \times 10^4$ | $6.6 \times 10^3$ |
| | | 100 ppm | $5.1 \times 10^6$ | $10.7 \times 10^3$ | $8.4 \times 10^3$ | $3.0 \times 10$ |
| 4 | ($R_1 = R_2 = R_3$ = octyl group) (X = Cl) | 1 ppm | $5.9 \times 10^6$ | 0 | 0 | 0 |
| | | 10 ppm | $5.9 \times 10^6$ | 0 | 0 | 0 |
| | | 100 ppm | $5.9 \times 10^6$ | 0 | 0 | 0 |
| 5 | ($R_1 = R_2$ = ethyl group) ($R_3$ = octyl group) (X = Cl) | 1 ppm | $6.5 \times 10^6$ | $3.0 \times 10^4$ | $2.0 \times 10^3$ | $8.5 \times 10^3$ |
| | | 10 ppm | $6.5 \times 10^6$ | $4.5 \times 10^3$ | $9.7 \times 10$ | 0 |
| | | 100 ppm | $6.5 \times 10^6$ | 0 | 0 | 0 |
| 6 | ($R_1 = R_2$ = butyl group) ($R_3$ = octyl group) (X = Cl) | 1 ppm | $6.5 \times 10^6$ | $2.0 \times 10^3$ | $1.4 \times 10$ | 0 |
| | | 10 ppm | $6.5 \times 10^6$ | $3.2 \times 10^2$ | $8.1 \times 10^2$ | 0 |
| | | 100 ppm | $6.5 \times 10^6$ | 0 | 0 | 0 |
| 7 | ($R_1 = R_2$ = phenyl group) ($R_3$ = dodecyl group) (X = Cl) | 1 ppm | $5.9 \times 10^6$ | $2.1 \times 10^4$ | $9.6 \times 10^3$ | 0 |
| | | 10 ppm | $5.9 \times 10^6$ | $3.0 \times 10^2$ | 0 | 0 |
| | | 100 ppm | $5.9 \times 10^6$ | 0 | 0 | 0 |

TABLE 3

Results of antibacterial activity test against *Escherichia coli* (IFO 3806)
(No. of bacteria /ml)

| Sample No. | Compound of Formula (I) | Concentration of Compound | Exposure Time (hours) | | | |
|---|---|---|---|---|---|---|
| | | | 0 | 0.5 | 1.0 | 2.0 |
| 1 | ($R_1 = R_2 = R_3$ = ethyl group) (X = Cl) | 1 ppm | $2.6 \times 10^6$ | $2.4 \times 10^6$ | $2.6 \times 10^6$ | $3.0 \times 10^6$ |
| | | 10 ppm | $2.6 \times 10^6$ | $3.1 \times 10^6$ | $2.7 \times 10^6$ | $2.5 \times 10^6$ |
| | | 100 ppm | $2.6 \times 10^6$ | $2.7 \times 10^5$ | $3.0 \times 10^4$ | $2.6 \times 10^3$ |
| 2 | ($R_1 = R_2 = R_3$ = butyl group) (X = Cl) | 1 ppm | $2.4 \times 10^6$ | $2.4 \times 10^6$ | $2.3 \times 10^6$ | $2.2 \times 10^6$ |
| | | 10 ppm | $2.4 \times 10^6$ | $2.7 \times 10^6$ | $2.7 \times 10^6$ | $2.0 \times 10^6$ |
| | | 100 ppm | $2.4 \times 10^6$ | $2.6 \times 10^5$ | $2.6 \times 10^4$ | $2.6 \times 10^3$ |
| 3 | ($R_1 = R_2 = R_3$ = phenyl group) (X = Cl) | 1 ppm | $2.5 \times 10^6$ | $3.1 \times 10^6$ | $2.3 \times 10^6$ | $2.6 \times 10^6$ |
| | | 10 ppm | $2.5 \times 10^6$ | $2.9 \times 10^6$ | $2.6 \times 10^4$ | $2.6 \times 10^4$ |
| | | 100 ppm | $2.5 \times 10^6$ | $2.4 \times 10^5$ | $2.5 \times 10^3$ | $2.5 \times 10^3$ |
| 4 | ($R_1 = R_2 = R_3$ = octyl group) (X = Cl) | 1 ppm | $1.7 \times 10^6$ | $8.5 \times 10^4$ | $2.5 \times 10^4$ | $3.2 \times 10^3$ |
| | | 10 ppm | $1.7 \times 10^6$ | 0 | 0 | 0 |
| | | 100 ppm | $1.7 \times 10^6$ | 0 | 0 | 0 |
| 5 | ($R_1 = R_2$ = ethyl group) ($R_3$ = octyl group) (X = Cl) | 1 ppm | $2.6 \times 10^6$ | $2.7 \times 10^5$ | $2.0 \times 10^4$ | $8.5 \times 10^3$ |
| | | 10 ppm | $2.6 \times 10^6$ | $2.4 \times 10^3$ | $9.8 \times 10^2$ | 0 |
| | | 100 ppm | $2.6 \times 10^6$ | 0 | 0 | 0 |
| 6 | ($R_1 = R_2$ = butyl group) ($R_3$ = octyl group) (X = Cl) | 1 ppm | $2.4 \times 10^6$ | $2.1 \times 10^5$ | $8.6 \times 10^3$ | $2.6 \times 10^3$ |
| | | 10 ppm | $2.4 \times 10^6$ | $1.5 \times 10$ | 0 | 0 |
| | | 100 ppm | $2.4 \times 10^6$ | 0 | 0 | 0 |
| 7 | ($R_1 = R_2$ = phenyl group) ($R_3$ = dodecyl group) (X = Cl) | 1 ppm | $2.5 \times 10^6$ | $7.5 \times 10^4$ | $2.0 \times 10^2$ | $8.7 \times 10^2$ |
| | | 10 ppm | $2.5 \times 10^6$ | 0 | 0 | 0 |
| | | 100 ppm | $2.5 \times 10^6$ | 0 | 0 | 0 |

Reference Example 2
(Synthesis of Phosphonium Salt Polymers)
Sample 8-15

Two grams (0.0563 mole) of tributyl-3 (and 4)-vinylbenzyl phosphonium chloride obtained by the same method as in Reference Example 1 were dissolved in 20 ml of water, and then 36.7 mg of 2,2'-azobis-(2-amidinopropane) hydrochloride was added to the solution, which was deaerated and sealed. After the solution was let stand at 60° C. for 6 hours to polymerize the compound, a large amount of tetrahydrofuran was poured into the solution, which was filtered to collect the precipitate separated out. Poly(tributyl-3 (and 4)-vinylbenzyl phosphonium chloride) of 0.97 g was obtained, whose degree of polymerization was 82.

Then, the same procedure was conducted using a variety of phosphine derivatives in place of tributyl phosphine to obtain the various polyvinylbenzyl phosphonium salt samples shown in Table 4.

TABLE 4

| Sample No. | Phosphine Derivative | Compound of Formula (I) |
|---|---|---|
| 8 | triethyl phosphine | poly (triethyl-3 (and 4)-vinylbenzyl phosphonium chloride) |
| 9 | tributyl phosphine | poly (tributyl-3 (and 4)-vinylbenzyl phosphonium chloride) |
| 10 | triphenyl phosphine | poly (triphenyl-3 (and 4)-vinylbenzyl phosphonium chloride) |
| 11 | trioctyl phosphine | poly (trioctyl-3 (and 4)-vinylbenzyl phosphonium chloride) |
| 12 | dodecyldimethyl phosphine | poly (dodecyldimethyl-3 (and 4)-vinylbenzyl phosphonium chloride) |
| 13 | tributyl phosphine | poly (tributyl-3 (and 4)-vinylbenzyl phosphonium tetrafluoroborate) |
| 14 | tributyl phosphine | poly (tributyl-3 (and 4)-vinylbenzyl phosphonium perchlorate) |

TABLE 4-continued

| Sample No. | Phosphine Derivative | Compound of Formula (I) |
| --- | --- | --- |
| 15 | tributyl phosphine | poly (tributyl-3 (and 4)-vinylbenzyl phosphonium hexafluorophosphate) |

Examples 8–15

*Staphylococcus aureus* (IFO 12732) as a typical Gram-positive bacteria and *Escherichia coli* (IFO 3806) as a typical Gram-negative bacteria were exposed by the samples of the various vinylbenzyl phosphonium salts samples of Table 4 at the different concentrations and exposure times shown in table 5 and 6 by the same method, and then the antibacterial activity was evaluated in the same manner as in the above Examples. The obtained results of antibacterial activity are shown in Tables 5 and 6.

TABLE 5

Results of antibacterial activity test against *Staphylococcus aureus* (IFO 12732) (No. of bacteria /ml)

| Sample No. | Compound of Formula (I) | Concentration of Compound | Exposure Time (hours) | | | |
| --- | --- | --- | --- | --- | --- | --- |
| | | | 0 | 0.5 | 1.0 | 2.0 |
| 8 | ($R_1 = R_2 = R_3$ = ethyl group) (X = Cl) | 1 ppm | $6.3 \times 10^6$ | $2.0 \times 10^4$ | $1.5 \times 10^4$ | $8.7 \times 10^3$ |
| | | 10 ppm | $6.3 \times 10^6$ | $3.5 \times 10^3$ | 0 | 0 |
| | | 100 ppm | $6.3 \times 10^6$ | 0 | 0 | 0 |
| 9 | ($R_1 = R_2 = R_3$ = butyl group) (X = Cl) | 1 ppm | $2.1 \times 10^7$ | $3.8 \times 10^4$ | $3.1 \times 10^4$ | $2.1 \times 10^4$ |
| | | 10 ppm | $2.1 \times 10^7$ | $1.0 \times 10^2$ | 0 | 0 |
| | | 100 ppm | $2.1 \times 10^7$ | 0 | 0 | 0 |
| 10 | ($R_1 = R_2 = R_3$ = phenyl group) (X = Cl) | 1 ppm | $1.0 \times 10^7$ | $3.2 \times 10^4$ | $8.1 \times 10^3$ | $1.3 \times 10^4$ |
| | | 10 ppm | $1.0 \times 10^7$ | 0 | 0 | 0 |
| | | 100 ppm | $1.0 \times 10^7$ | 0 | 0 | 0 |
| 11 | ($R_1 = R_2 = R_3$ = octyl group) (X = Cl) | 1 ppm | $4.5 \times 10^6$ | $1.1 \times 10^4$ | $4.0 \times 10^3$ | $2.9 \times 10^3$ |
| | | 10 ppm | $4.5 \times 10^6$ | 0 | 0 | 0 |
| | | 100 ppm | $4.5 \times 10^6$ | 0 | 0 | 0 |
| 12 | ($R_1 = R_2$ = methyl group) ($R_3$ = dodecyl group) (X = Cl) | 1 ppm | $7.8 \times 10^6$ | $2.3 \times 10^4$ | $7.6 \times 10^3$ | $5.5 \times 10^3$ |
| | | 10 ppm | $7.8 \times 10^6$ | 0 | 0 | 0 |
| | | 100 ppm | $7.8 \times 10^6$ | 0 | 0 | 0 |
| 13 | ($R_1 = R_2 = R_3$ = butyl group) (X = $BF_4$) | 1 ppm | $1.0 \times 10^7$ | $3.5 \times 10^4$ | $2.9 \times 10^4$ | $1.8 \times 10^4$ |
| | | 10 ppm | $1.0 \times 10^7$ | $3.0 \times 10^2$ | 0 | 0 |
| | | 100 ppm | $1.0 \times 10^7$ | 0 | 0 | 0 |
| 14 | ($R_1 = R_2 = R_3$ = butyl group) (X = $ClO_4$) | 1 ppm | $8.3 \times 10^6$ | $2.7 \times 10^4$ | $1.6 \times 10^4$ | $1.4 \times 10^4$ |
| | | 10 ppm | $8.3 \times 10^6$ | $1.8 \times 10^2$ | 0 | 0 |
| | | 100 ppm | $8.3 \times 10^6$ | 0 | 0 | 0 |
| 15 | ($R_1 = R_2 = R_3$ = butyl group) (X = $PF_6$) | 1 ppm | $1.1 \times 10^7$ | $4.0 \times 10^4$ | $3.2 \times 10^4$ | $2.2 \times 10^4$ |
| | | 10 ppm | $1.1 \times 10^7$ | $2.7 \times 10^2$ | 0 | 0 |
| | | 100 ppm | $1.1 \times 10^7$ | 0 | 0 | 0 |

TABLE 6

Results of antibacterial activity test against *Escherichia coli* (IFO 3806) (No. of bacteria /ml)

| Sample No. | Compound of Formula (I) | Concentration of Compound | Exposure Time (hours) | | | |
| --- | --- | --- | --- | --- | --- | --- |
| | | | 0 | 0.5 | 1.0 | 2.0 |
| 8 | ($R_1 = R_2 = R_3$ = ethyl group) (X = Cl) | 1 ppm | $2.2 \times 10^6$ | $1.6 \times 10^6$ | $1.1 \times 10^6$ | $4.5 \times 10^5$ |
| | | 10 ppm | $2.2 \times 10^6$ | $1.8 \times 10^6$ | $1.3 \times 10^6$ | $9.6 \times 10^5$ |
| | | 100 ppm | $2.2 \times 10^6$ | $1.7 \times 10^5$ | $1.5 \times 10^4$ | $9.0 \times 10^3$ |
| 9 | ($R_1 = R_2 = R_3$ = butyl group) (X = Cl) | 1 ppm | $2.0 \times 10^6$ | $1.1 \times 10^6$ | $7.7 \times 10^5$ | $7.7 \times 10^5$ |
| | | 10 ppm | $2.0 \times 10^6$ | $1.4 \times 10^6$ | $1.2 \times 10^6$ | $8.7 \times 10^5$ |
| | | 100 ppm | $2.0 \times 10^6$ | $1.1 \times 10^4$ | $7.2 \times 10^4$ | $9.2 \times 10^3$ |
| 10 | ($R_1 = R_2 = R_3$ = phenyl group) (X = Cl) | 1 ppm | $3.0 \times 10^6$ | $1.2 \times 10^6$ | $4.7 \times 10^5$ | $6.8 \times 10^5$ |
| | | 10 ppm | $3.0 \times 10^6$ | $1.8 \times 10^6$ | $1.4 \times 10^6$ | $9.6 \times 10^5$ |
| | | 100 ppm | $3.0 \times 10^6$ | $2.1 \times 10^5$ | $1.8 \times 10^3$ | $1.5 \times 10^2$ |
| 11 | ($R_1 = R_2 = R_3$ = octyl group) (X = Cl) | 1 ppm | $2.0 \times 10^6$ | $7.7 \times 10^5$ | $2.4 \times 10^5$ | $6.2 \times 10^4$ |
| | | 10 ppm | $2.0 \times 10^6$ | 0 | 0 | 0 |
| | | 100 ppm | $2.0 \times 10^6$ | 0 | 0 | 0 |

Reference Example 3
(Synthesis of Phosphonium Salt Copolymers)
Sample 16

In 10 g of dimethylformamide were dissolved 1.5 g (0.0042 mole) of tributyl-3 (and 4)-vinylbenzyl phosphonium chloride (A), and 0.31 g (0.0043 mole) of acrylamide (B), and then 18.1 mg of azobisisobutyl nitrile were added to the solvent, which was deaerated and sealed. After the solvent was let stand at 60° C. for 6 hours to polymerize the compounds, the resulting polymer was poured into an excess amount of acetone, which was filtered to collect the precipitate separated out. A copolymer (1.11 g) of tributyl-3 (and 4)-vinylbenzyl phosphonium chloride/acrylamide was obtained, whose weight-average molecular weight was 10,500.

Sample 17

In 10 g of water were dissolved 0.5 g (0.0014 mole) of tributyl-3 (and 4)-vinylbenzyl phosphonium chloride (A), and 1.5 g (0.0211 mole) of acrylamide (B), and then 18.0 mg of 2,2'-azobis-2-amidinopropane hydrochloride were added to the solution, which was deaerated and sealed. After the solution was let stand at 60° C. for 6 hours to polymerize the compounds, the resulting polymer was poured into an excess amount of a mixture of diethylether and acetone (1:1), which was filtered to collect the precipitate out. A copolymer (1.64 g) of tributyl-3 (and 4)-vinylbenzyl phosphonium chloride/acrylamide was obtained.

Sample 18

In 10 g of dimethylformamide were dissolved 1.5 g (0.0042 mole) of tributyl-3 (and 4)-vinylbenzyl phosphonium chloride (A), and 0.47 g (0.0043 mole) of N-vinyl-2-pyrrolidone (B), and then 17.6 mg of azobisisobutyl nitrile were added to the solvent, which was deaerated and sealed. After the solvent was let stand at 60° C. for 6 hours to polymerize the compounds, the resulting polymer was poured into an excess amount of tetrahydrofuran, which was filtered to collect the precipitate separated out. A copolymer (1.40 g) of tributyl-3 (and 4)-vinylbenzyl phosphonium chloride/N-vinyl-2-pyrrolidone was obtained, whose weight-average molecular weight was 17,400.

Sample 19

In 10 g of dimethylformamide were dissolved 0.5 g (0.0014 mole) of tributyl-3 (and 4)-vinylbenzyl phosphonium chloride (A), and 1.5 g (0.0135 mole) of N-vinyl-2-pyrrolidone (B), and then 18.0 mg of azobisisobutyl nitrile were added to the solvent, which was deaerated and sealed. After the solvent was let stand at 60° C. for 6 hours to polymerize the compounds, the resulting polymer was poured into an excess amount of diethyl ether, which was filtered to collect the precipitate separated out. A copolymer (1.09 g) of tributyl-3 (and 4)-vinylbenzyl phosphonium chloride/N-vinyl-2-pyrrolidone was obtained.

Sample 20

In 10 g of dimethylformamide were dissolved 1.51 g (0.0043 mole) of tributyl-3 (and 4)-vinylbenzyl phosphonium chloride (A), and 0.44 g (0.0042 mole) of styrene (B), and then 18.0 mg of azobisisobutyl nitrile were added to the solvent, which was deaerated and sealed. After the solvent was let stand at 60° C. for 6 hours to polymerize the compounds, the resulting polymer was poured into an excess amount of tetrahydrofuran, which was filtered to collect the precipitate separated out. A copolymer (0.82 g) of tributyl-3 (and 4)-vinylbenzyl phosphonium chloride/styrene was obtained, whose weight-average molecular weight was 9,400.

Sample 21

In 10 g of dimethylformamide were dissolved 0.5 g (0.0014 mole) of tributyl-3 (and 4)-vinylbenzyl phosphonium chloride (A), and 1.5 g (0.0144 mole) of styrene (B), and then 18.0 mg of azobisisobutyl nitrile were added to the solvent, which was deaerated and sealed. After the solvent was let stand at 60° C. for 6 hours to polymerize the compounds, the resulting polymer was poured into an excess amount of tetrahydrofuran, which was filtered to collect the precipitate separated out. A copolymer (0.47 g) of tributyl-3 (and 4)-vinylbenzyl phosphonium chloride/styrene was obtained.

Then, the mole % and degree of polymerization of structural units (A) and (B) in the samples 16–21 of the phosphonium salt copolymers obtained from the above mentioned syntheses are shown in the following Table 7.

TABLE 7

| Sample No. | Mole % unit (A) | Mole % unit (B) | Degree of Polymerization unit (A) | Degree of Polymerization unit (B) |
|---|---|---|---|---|
| 16 | 73 | 27 | 21.6 | 39.9 |
| 17 | 7 | 93 | 2.1 | 137.4 |
| 18 | 89 | 11 | 43.6 | 17.2 |
| 19 | 19 | 81 | 9.3 | 126.8 |
| 20 | 80 | 20 | 21.2 | 18.0 |
| 21 | 17 | 83 | 4.5 | 74.9 |

Examples 16–21

*Staphylococcus aureus* (IFO 12732) as a typical Gram-positive bacteria was exposed to the various samples of copolymers obtained from Reference Example 3 above at the different concentrations and exposure times shown in Table 8 following. Antibacterial activity was evaluated by the serial dilution method. The obtained results of the antibacterial activity test are shown in Table 8.

TABLE 8

Results of antibacterial activity test against *Staphylococcus aureus* (IFO 12732) (No. of bacteria /ml)

| Sample No. | Phosphonium Salt Series Copolymer | Concentration of Compound | Exposure Time (hours) 0 | 0.5 | 1.0 | 2.0 |
|---|---|---|---|---|---|---|
| 16 | ($R_1 = R_2 = R_3$ = butyl group) ($X$ = Cl) | 1 ppm | $1.4 \times 10^7$ | $1.6 \times 10^4$ | $7.4 \times 10^3$ | $5.0 \times 10^3$ |
|  |  | 10 ppm | $1.4 \times 10^7$ | 0 | 0 | 0 |
|  |  | 100 ppm | $1.4 \times 10^7$ | 0 | 0 | 0 |
| 17 | ($R_1 = R_2 = R_3$ = butyl group) ($X$ = Cl) | 1 ppm | $0.9 \times 10^7$ | $1.5 \times 10^5$ | $1.4 \times 10^5$ | $7.5 \times 10^4$ |
|  |  | 10 ppm | $0.9 \times 10^7$ | $6.7 \times 10^3$ | $5.6 \times 10^3$ | $3.2 \times 10^3$ |
|  |  | 100 ppm | $0.9 \times 10^7$ | $2.3 \times 10^3$ | 0 | 0 |
| 18 | ($R_1 = R_2 = R_3$ = butyl group) ($X$ = Cl) | 1 ppm | $1.1 \times 10^7$ | $2.3 \times 10^4$ | $2.0 \times 10^4$ | $1.3 \times 10^4$ |
|  |  | 10 ppm | $1.1 \times 10^7$ | 0 | 0 | 0 |
|  |  | 100 ppm | $1.1 \times 10^7$ | 0 | 0 | 0 |
| 19 | ($R_1 = R_2 = R_3$ = butyl group) ($X$ = Cl) | 1 ppm | $1.0 \times 10^7$ | $8.0 \times 10^4$ | $4.5 \times 10^4$ | $2.5 \times 10^4$ |
|  |  | 10 ppm | $1.0 \times 10^7$ | $1.0 \times 10^2$ | 0 | 0 |
|  |  | 100 ppm | $1.0 \times 10^7$ | 0 | 0 | 0 |
| 20 | ($R_1 = R_2 = R_3$ = butyl group) ($X$ = Cl) | 1 ppm | $1.2 \times 10^7$ | $1.5 \times 10^5$ | $8.7 \times 10^4$ | $5.0 \times 10^4$ |
|  |  | 10 ppm | $1.2 \times 10^7$ | 0 | 0 | 0 |
|  |  | 100 ppm | $1.2 \times 10^7$ | 0 | 0 | 0 |
| 21 | ($R_1 = R_2 = R_3$ = butyl group) ($X$ = Cl) | 1 ppm | $1.2 \times 10^7$ | $3.0 \times 10^5$ | $1.4 \times 10^5$ | $8.9 \times 10^5$ |
|  |  | 11 ppm | $1.2 \times 10^7$ | $1.5 \times 10^3$ | 0 | 0 |
|  |  | 100 ppm | $1.2 \times 10^7$ | $2.0 \times 10^2$ | 0 | 0 |

As illustrated above, it has been found that the vinylbenzyl phosphonium salts of the present invention and phosphonium salt polymers and copolymers in which the vinylbenzyl phosphonium salts, a monomer, are polymerized have excellent antibacterial activity.

INDUSTRIAL APPLICABILITY

The antibacterial agents of the present invention are useful because of their strong anti-microorganism activity. The antibacterial agents of the present invention may be applied to, for example, external antibacterial agents, antibacterial agents for hygienically processing textiles, cloth and the like, and for medical devices, coatings, constructional materials, pools, industrial water, and the like. Further, they may also be provided with antistatic properties, fire resistance and stain resistance. The compounds of the present invention and copolymers thereof can be used in the forms of spheres and pellets, and as filters. They may also be used as various industrial materials having antibacterial activity by processing them.

What is claimed is:

1. A method for providing antibacterial property to an object in need thereof, comprising contacting said object with an effective amount of a bactericidal composition comprising a vinyl benzyl phosphonium salt of formula (1)

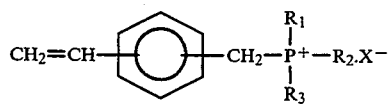

wherein $R_1$, $R_2$ and $R_3$ each, independently, represent a hydrogen atom, a linear or branched alkyl group having 1–18 carbon atoms, an aryl group, a hydroxyl group, or an alkoxyl-substituted alkyl, aryl or aralkyl group and $X^-$ is an anion; a phosphonium salt polymer prepared by polymerization of said vinyl benzyl phosphonium salt, or a mixture thereof.

2. The method as claimed in claim 1, wherein said vinylbenzyl phosphonium salt is trioctyl vinylbenzyl phosphonium salt.

3. The method as claimed in claim 1, wherein said phosphonium salt polymer is a homopolymer of phosphonium salt of the formula (II),

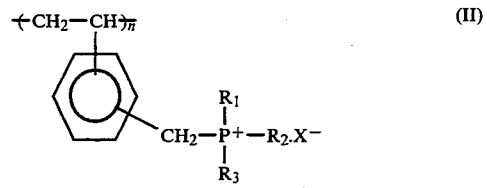

wherein $R_1$, $R_2$ and $R_3$ each, independently, represent a hydrogen atom, a linear or branched alkyl group having 1–18 carbon atoms, an aryl group, a hydroxyl group, or an alkoxyl-substituted alkyl, aryl or aralkyl group; $X^-$ is an anion; and n is an integer or 2 or more.

4. The method as claimed in claim 1, wherein said phosphonium salt polymer is a copolymer of the vinyl-benzyl phosphonium salt of formula (I) and another vinyl monomer capable of copolymerizing therewith.

* * * * *